US007772211B2

(12) United States Patent
Tsai et al.

(10) Patent No.: US 7,772,211 B2
(45) Date of Patent: *Aug. 10, 2010

(54) PRODUCTION OF CARRAGEENAN AND CARRAGEENAN PRODUCTS

(75) Inventors: Albert G. Tsai, New Castle, DE (US); Linnea K. S. Ledwith, Rockport, ME (US); Robert Kopesky, Camden, ME (US); Maurice Gerard Lynch, Waterloo (BE); William Ross Blakemore, Topsham, ME (US); Peter J. Riley, Yardley, PA (US)

(73) Assignee: FMC Corporation, Philadelphia, PA (US)

( * ) Notice: Subject to any disclaimer, the term of this patent is extended or adjusted under 35 U.S.C. 154(b) by 616 days.

This patent is subject to a terminal disclaimer.

(21) Appl. No.: 11/542,936

(22) Filed: Oct. 4, 2006

(65) Prior Publication Data

US 2007/0112184 A1  May 17, 2007

Related U.S. Application Data

(60) Division of application No. 10/450,107, filed as application No. PCT/US01/47020 on Dec. 10, 2001, now Pat. No. 7,189,843, which is a continuation-in-part of application No. 09/798,012, filed on Mar. 2, 2001, now Pat. No. 6,479,649.

(60) Provisional application No. 60/255,279, filed on Dec. 13, 2000.

(51) Int. Cl.
*A61K 31/731* (2006.01)
*C07H 1/06* (2006.01)
*C07H 1/08* (2006.01)

(52) U.S. Cl. .................................. 514/54; 536/123.1
(58) Field of Classification Search .............. None
See application file for complete search history.

(56) References Cited

U.S. PATENT DOCUMENTS

| | | | |
|---|---|---|---|
| 2,620,334 A | 12/1952 | Nielson et al. | |
| 2,620,335 A | 12/1952 | Nielson et al. | |
| 2,624,727 A | 1/1953 | Le Gloahec | |
| 3,094,517 A | 6/1963 | Stanley | |
| 3,176,003 A | 3/1965 | Stancioff | |
| 3,280,102 A | 10/1966 | Gordon et al. | |
| 3,342,612 A | 9/1967 | Foster et al. | |
| 3,849,395 A | 11/1974 | Moirano et al. | |
| 3,855,149 A | 12/1974 | Bielskis | |
| 3,901,873 A | 8/1975 | Doi et al. | |
| 3,907,770 A | 9/1975 | Strong | |
| 4,112,223 A | 9/1978 | Lin et al. | |
| 4,443,486 A | 4/1984 | Guiseley | |
| 4,765,886 A | 8/1988 | Whitaker | |
| 4,816,278 A | 3/1989 | Sasmoto et al. | |
| 4,851,394 A | 7/1989 | Kudodera | |
| 4,859,484 A | 8/1989 | Bielskis et al. | |
| 4,950,752 A | 8/1990 | Whitaker | |
| 5,089,307 A | 2/1992 | Ninomiya et al. | |
| 5,275,803 A | 1/1994 | Dawson | |
| 5,275,834 A | 1/1994 | Thibault et al. | |
| 5,342,626 A | 8/1994 | Winson, Jr. et al. | |
| 5,496,936 A | 3/1996 | Thami et al. | |
| 5,502,179 A | 3/1996 | Larsen | |
| 5,662,840 A | 9/1997 | Thomas et al. | |
| 5,756,123 A | 5/1998 | Yamamoto et al. | |
| 5,777,102 A * | 7/1998 | Larsen .................... 536/124 | |
| 5,801,240 A | 9/1998 | Rideout et al. | |
| 6,042,854 A | 3/2000 | Morris et al. | |
| 6,045,780 A * | 4/2000 | Bixler et al. ............. 424/49 | |
| 6,063,915 A | 5/2000 | Hansen et al. | |
| 6,146,570 A | 11/2000 | Stern et al. | |
| 6,214,376 B1 | 4/2001 | Gennadios | |
| 6,268,191 B1 | 7/2001 | Prud'homme et al. | |
| 6,331,205 B1 | 12/2001 | Paris et al. | |
| 6,375,981 B1 | 4/2002 | Gilleland et al. | |
| 6,387,354 B1 | 5/2002 | Bixler et al. | |
| 6,479,649 B1 * | 11/2002 | Tsai et al. ............. 536/1.11 | |
| 6,528,088 B1 | 3/2003 | Gilleland et al. | |
| 6,582,727 B2 | 6/2003 | Tanner et al. | |
| 6,635,275 B1 | 10/2003 | Scott et al. | |
| 6,685,978 B1 * | 2/2004 | Hauksson ............. 426/573 | |
| 7,018,635 B2 * | 3/2006 | Tsai et al. ............. 424/195.18 | |

(Continued)

FOREIGN PATENT DOCUMENTS

CL  125-96  9/1996

(Continued)

OTHER PUBLICATIONS

Stancioff D, Carrageenans: Versatile Food Ingredients, *Foods Food Ingredients J Japan*, 167, 37-47, 1996.

(Continued)

*Primary Examiner*—Eric S Olson

(57) ABSTRACT

The methods of the present invention prepare carrageenan products from processed seaweed material having a solids content of less than 25% by weight solids, using shear stress treatment. The carrageenan products comprise at least about 60% by weight of carrageenan and at least about 2% by weight of acid insoluble material. The carrageenan products of the present invention are useful as components in food products, such as, dairy products, meats, and dessert gels as well as non-food products, such as, toothpaste formulations, cosmetics, paints, films and delivery capsules.

5 Claims, 1 Drawing Sheet

U.S. PATENT DOCUMENTS

| | | | |
|---|---|---|---|
| 7,189,843 B2 * | 3/2007 | Tsai et al. .................. | 536/114 |
| 2002/0071861 A1 | 6/2002 | Blanchin et al. | |

FOREIGN PATENT DOCUMENTS

| EP | 0432835 | * | 6/1991 |
|---|---|---|---|
| EP | 0 598 141 A1 | | 5/1994 |
| EP | 0 812 545 A | | 12/1997 |
| EP | 0812545 | * | 12/1997 |
| JP | 11252 | | 8/1958 |
| JP | S48-091256 | | 11/1973 |
| JP | 55-12234 | | 3/1980 |
| JP | S55-12234 | | 3/1980 |
| JP | S57-20875 | | 12/1982 |
| JP | S59-179502 | | 10/1984 |
| JP | S60-055039 | | 3/1985 |
| JP | 61254146 | | 11/1986 |
| JP | S62-29947 | | 2/1987 |
| JP | S62-186754 | | 8/1987 |
| JP | S63-164858 | | 7/1988 |
| JP | S63-216442 | | 9/1988 |
| JP | H1-211463 | | 8/1989 |
| JP | H03-012231 | | 1/1991 |
| JP | H03-053873 | | 3/1991 |
| JP | 2 572611 | | 1/1997 |
| JP | H10-025302 | | 1/1998 |
| WO | WO 84/00761 | | 3/1984 |
| WO | WO 90/04333 | | 5/1990 |
| WO | WO 94/22921 | | 10/1994 |
| WO | WO 94/22922 | | 10/1994 |
| WO | WO 98/40412 | | 9/1998 |
| WO | WO 99/47249 | | 9/1999 |
| WO | WO 00/06609 | | 2/2000 |
| WO | WO 00/10538 | | 3/2000 |
| WO | WO 01/03677 | | 1/2001 |
| WO | WO 01/66073 A2 | | 9/2001 |

OTHER PUBLICATIONS

DeRuiter G, Carrageenan Biotechnology, *Trends in Food Science & Tech* 8(12)389-395, Dec. 1997.

Prakash, J., "Proceedings of the Regional Workshop on Seaweed Culture and Marketing," South Pacific Aquaculture Development Project, Adams, T., et al. (Eds.), Nov. 14-17, 1989, 1-86.

Stanley, N., "Chapter 3: Production, properties and uses of carrageenan," Food and Agriculture Organization of the United Nations, FAO Fisheries Technical Paper No. 288, McHugh, D.J. (Ed.), 1987, 116-146.

Meiji, et al., "Treating seaweed to enable utilisation of components - by crushing, adjusting water content and extruding," Derwent Publications Ltd., London, XP002196719, Nov. 28, 1973. 1 page (Abstract).

PCT International Search Report dated Jun. 11, 2002 (PCT/US01/47020).

* cited by examiner

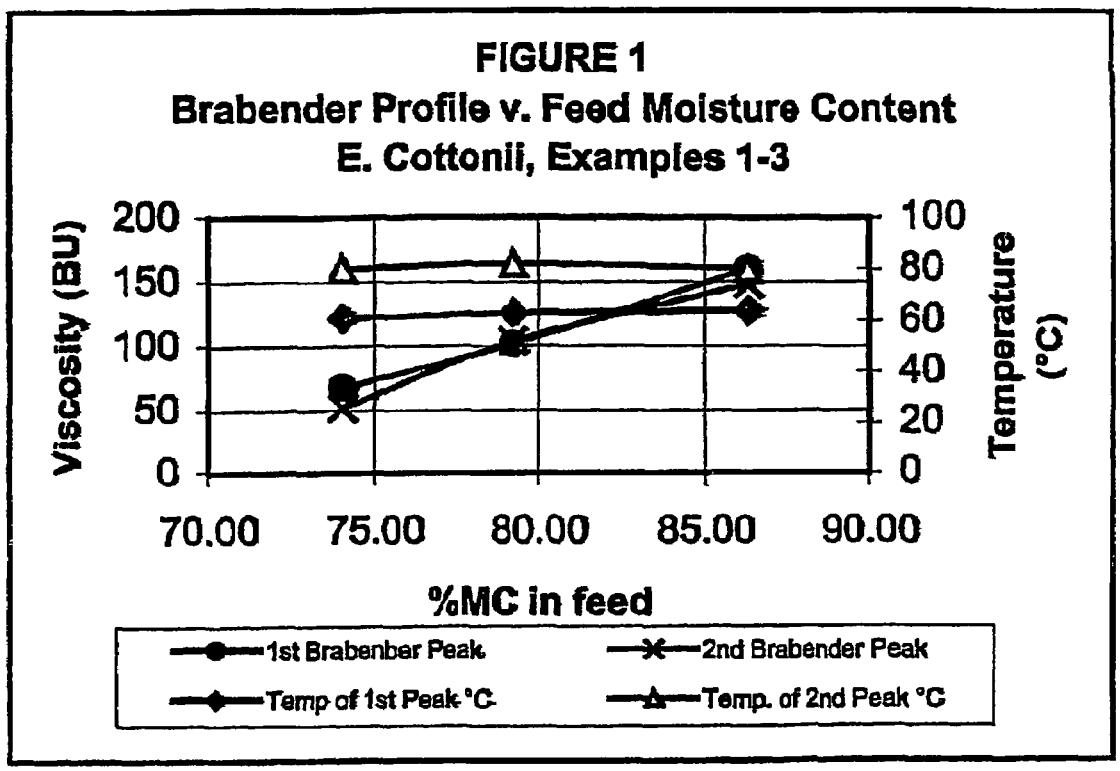

PRODUCTION OF CARRAGEENAN AND CARRAGEENAN PRODUCTS

RELATED APPLICATIONS

This application is a divisional application of U.S. application Ser. No. 10/450,107, filed Oct. 14, 2003 now U.S. Pat. No. 7,189,843 allowed May 9, 2006, incorporated herein by reference, which is the U.S. National Phase or PCT/US01/47020, filed Dec. 10, 2001, which is a continuation in part of U.S. application Ser. No. 09/789,012, filed Mar. 2, 2001 now U.S. Pat. No. 6,479,649 which claims priority on U.S. Provisional Application 60/255,279, filed Dec. 13, 2000.

FIELD OF THE INVENTION

The present invention is directed to carrageenan products, methods of preparing such carrageenan products, and to formulations containing carrageenan products according to the present invention.

BACKGROUND OF THE INVENTION

Carrageenan is a complex mixture of sulfated polysaccharides comprising linear polymers of 1,3 bound α-D-galactose units and 1,4 bound α-D-galactose units with the general formula:

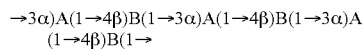

wherein A and B represent galactose residues derived from two different groups.

Carrageenan is extracted from red seaweeds and constitutes the principal structure of the seaweed. It is located within the cell wall and intracellular matrix of the plant tissue. The carrageenan content of commercially harvested seaweeds is generally between 30% and 80% based on the seaweed dry weight.

Carrageenan finds wide applicability as a food ingredient and is functional in foods such as dairy products, water dessert gels, meat products, confections, beverages, dressings and other such products. Carrageenan is also used in non-food products such as cosmetics, toothpaste, and other personal care products. The molecular weight of commercial carrageenan products is typically from about 100,000 to 1,000,000 Daltons. Carrageenans have the unique ability to form an almost infinite variety of gels at room temperature, with a variety of gelling and melting points. These gels require no refrigeration, and can be made stable through repeated freeze-thaw cycles. Carrageenan solutions can thicken, suspend, and stabilize particulates, colloidal dispersions and water/oil emulsions. The solutions shear thin, which allows them to be pumped easily. Also, the solutions rapidly rebuild viscosity and suspending power on standing. Depending upon the food application, carrageenan present in a few percent by weight or less provides gelling, thickening, and binding, and also helps in imparting appropriate texture to the food product. Owing to these qualities, carrageenan is particularly desirable as a fat replacement in low fat foods.

Carrageenan is generally soluble in warm water, in which it forms viscous solutions. It is insoluble in most organic solvents, and typically forms complexes with proteins. The major types of carrageenan are designated as kappa, iota, lambda, nu and mu. These are differentiated based on the nature of the repeating galactose units contained in the carrageenan. The polymer chains in carrageenan can be cleaved by hydrolytic depolymerization upon treatment with an acid, or by oxidative depolymerization upon treatment with hydrogen peroxide. Upon cleavage of the polymer chains, carrageenan products having optimum gelling properties and viscosity can be obtained.

In a typical process for making pure carrageenan, crude seaweed is first washed with cold water to remove sand and other particulates that may be present after the seaweed has been harvested. Carrageenan typically does not swell during the cold wash, primarily because carrageenan in seaweed is associated with the structural components of the seaweed, generally cellulose. Depending on the seaweed species, following the cold wash a hot water extraction procedure is typically performed in which the extracted carrageenan is treated with aqueous base at high temperature. Generally, the base used is an alkali or alkaline earth metal hydroxide such as, for example, NaOH, Ca(OH)$_2$, or KOH. This high temperature aqueous base modification leads to the formation of 3,6-anhydro linkages in the galactose units of the carrageenan polysaccharide. After base modification, the hot extract is filtered to remove insoluble material such as cellulose, hemicellulose and other particulates, and acid is added to adjust the pH to 9 or lower. The filtrate can then be concentrated to about 4% carrageenan for further processing. Optional procedural steps after extraction may include centrifugation and bleaching. Pure carrageenan is typically obtained by precipitation of the extract from the aqueous solution with KCl or an alcohol such as isopropanol.

Preparation of pure carrageenan by extraction on a commercial scale is expensive because of viscosity and gelling properties that limit the rate at which such carrageenan products can be processed. After the extraction step, a hot aqueous stream can typically only contain low concentrations of carrageenan, typically up to about 4%. At higher concentrations of carrageenan, the aqueous stream becomes too viscous to be processed efficiently. Therefore, a relatively low proportion of carrageenan is obtained per unit volume of the aqueous process stream.

There has been an ongoing search for more cost-effective methods of preparing semi-refined carrageenan and other products as lower cost replacements for conventional carrageenan. Semi-refined carrageenan (SRC) products are those in which few or none of the structural components of the seaweed, principally cellulose, have been removed. During the preparation of SRC, a salt such as KCl or NaCl typically is added during base modification along with the base. The presence of sufficient amounts of salt prevents disintegration of the seaweed structure and inhibits extraction of carrageenan from the seaweed. An alcohol, such as isopropanol, can also be used to inhibit extraction during the high temperature base modification step. Following the base modification step, with the seaweed structure still intact, the processed seaweed mixture is typically dried to afford SRC. When the seaweed is a member of the Eucheuma family, the SRC obtained is known as processed *Eucheuma* seaweed (PES).

U.S. Pat. No. 5,502,179 is directed to processes wherein the seaweed starting (feed) material is mixed with a base and a solvent in which carrageenan is insoluble. This base-treated mixture is washed with an aqueous solution and then subjected to shear stress treatment (such as an extrusion process or by means of a shear mixer). The shear stress treatment is said to be performed on seaweed material having a solids content of at least 25%, at a temperature between 100°C and 175° C., for about 10 to 200 seconds. The carrageenan material resulting from the shear stress treatment may be dried and subjected to comminution, grinding or milling to obtain a powder with a particle size in the range of 0.05 to 0.5 mm.

Conventional carrageenans typically have some advantages relative to SRC obtained from the same seaweed. One such advantage is that they typically begin to hydrate, i.e., they begin to swell and solubilize, at a lower temperatures than does SRC. For example, conventional iota carrageenan obtained from *Eucheuma spinosum* will hydrate, swell, and solubilize at room temperature. PES derived from *Eucheuma spinosum*, however, does not hydrate, swell and solubilize until first heated to above about 60° C. Another such advantage is that because SRC contains cellulosic and other materials which are absent in conventional carrageenan, gels formed from SRC have reduced clarity relative to pure carrageenan gels. Therefore, utility of SRC products has been limited to those applications where the food product is not required to be clear and can be readily prepared at the high temperatures required for hydration and solubility of carrageenan to occur. For many applications, however, it is desirable to have an SRC which provides gelling without the need for such high temperatures. It is also important that SRC have acceptable color and appearance suitable for use in products made for human consumption such as, for example, cream, ice cream, other dairy products, and beverages, as well as non-food products such as, for example, cosmetics, tooth paste, and other personal care products.

Therefore, there is a need in the art for a low cost processes for producing carrageenan products with improved hydration characteristics while maintaining acceptable color and appearance suitable for use in food products.

SUMMARY OF THE INVENTION

The present invention provides methods for preparing a carrageenan product comprising the steps of providing a carrageenan-containing seaweed material having a seaweed solids content of less than 25% by weight, and subjecting this seaweed material to shear stress treatment. The carrageenan-containing seaweed material optionally is treated with base prior to extrusion.

In one embodiment, the carrageenan-containing seaweed material is prepared by a process comprising the steps of washing the seaweed with water to produce washed seaweed; rinsing the seaweed with water to form rinsed seaweed; and washing the rinsed seaweed with water or an aqueous solution to form the carrageenan-containing seaweed material.

In another embodiment, the methods of the present invention comprise washing the seaweed with water, treating the seaweed with a base at a temperature of about 25° C. to about 65° C. to form base-modified seaweed; rinsing the base-modified seaweed with water, washing this base-modified seaweed with an aqueous solution of a salt; rinsing this base-modified seaweed with water to form processed seaweed, wherein the processed seaweed comprises less than 25% solids; extruding this processed seaweed to form extruded seaweed; and drying the extruded seaweed to form a carrageenan product.

In yet another embodiment, the concentration of the aqueous salt solution is less than about 40%. It is preferred that the concentration of the aqueous salt solution be less than about 15%. It is more preferred that the concentration of the aqueous salt solution be between about 2% and about 15%.

The present invention also includes carrageenan products that preferably comprise at least about 60% by weight of carrageenan and at least about 2% by weight of acid insoluble material, and have an onset of hydration below about 50° C. In a preferred embodiment, the carrageenan product is derived from *Eucheuma spinosum*, or any other species containing iota-carrageenan. In another preferred embodiment, the carrageenan product further comprises about 2% to about 15% by weight of a salt. A preferred salt is sodium chloride.

The present invention further includes foods and other products containing a carrageenan product or products produced by the foregoing methods. The carrageenan product preferably comprises at least about 60% by weight of carrageenan and at least about 2% by weight of acid insoluble material. For such carrageenan products produced from *Eucheuma cottonii*, the onset of hydration can be as low as below about 50° C. For such carrageenan products produced from *Eucheuma spinosum*, the onset of hydration can be as low as below about 30° C.

Other products include toothpaste formulations comprising a binder, a humectant, an abrasive, and water, wherein the binder is a carrageenan product according to the present invention. It is preferred that the concentration of the binder be from about 0.5 to about 1.5% by weight of the toothpaste formulation.

The present invention further includes methods of making articles containing one or more carrageenan products produced by the methods of the invention. In one embodiment, a solution comprising the carrageenan-containing product of the invention is heated and at least a portion of the heated solution is then subjected to conditions effective to transform it into a barrier material. Films can be formed, for example, by casting the solution on a cooled rotating drum. Optionally, the carrageenan-containing film can be fed through a series of rollers to counter rotating dies which form, cut, and fill capsules of various sizes.

BRIEF DESCRIPTION OF THE DRAWINGS

FIG. 1 is a graph showing changes in the Brabender profile with varying levels of feed moisture content.

DETAILED DESCRIPTION OF THE INVENTION

The present invention is directed to processes for preparing carrageenan-containing products from processed seaweed using shear stress. Representative seaweed species include those from the Eucheuma, Gigartina, Chondrus, and Irideae families. Preferred species include *Eucheuma spinosum*, *Eucheuma cottonii*, and *Gigartina radula*.

Processed seaweed can be obtained by treatment of the seaweed with a base, followed by neutralization, if needed. Base modification of the crude seaweed is optional and can be performed with a base such as NaOH, KOH, or $Ca(OH)_2$ in the presence of a salt such as NaCl, or KCl. Subsequent aqueous rinses of the modified seaweed can contain salt. As used herein, the term "salt" refers to the reaction product obtained when a metal displaces a hydrogen atom of an acid. In the present invention, the salt may be used in the form of an aqueous solution. If a salt is to be used in the rinses; it is preferable to use the same salt as was used in the base modification procedure. Use of a sodium salt, instead of a potassium salt, typically affords a final, shear-stressed product having improved water solubility.

The carrageenan-containing seaweed feed material obtained prior to shear stress treatment is dried, or is either semi-dried or wet and has a solids content of less than 25%. As used herein, the term "solids content" is the difference between the total weight and the weight of the moisture or water content in the seaweed material mixture. The water content of the seaweed material prior to extrusion includes water that may be bound to the seaweed material (as water of hydration), or water that has been added to the seaweed material.

In some instances, such as, for example, where the carrageenan containing seaweed feed material is obtained dry, it is typically necessary to add water to the dried seaweed material to reconstitute it before extrusion.

It has been observed that when a feedstream of seaweed material has a solids content of 25% or higher, shear stress treatment typically results in an unacceptable darkening of the material. The color of a carrageenan product is typically very important to an end user. End users who prepare products for human consumption, for example, typically select SRC products that are no darker than off-white, with cheaper, more deeply-colored products often finding their way into products in which color is not such a concern.

While not fully understood, the differences that are observed with respect to feedstreams having more than 25% solids may be due to the effect that the water has on the heat generated by the shear stress to which the feedstreams are exposed. Water tends to dissipate heat created during the extrusion away from the seaweed material, decreasing the extent to which the heat is available to caramelize sugars in the feedstock, thereby darkening the final product. Thus, where there is more water to dissipate heat, lighter products are produced.

Color changes that occur during shear stress treatment can be monitored with the human eye or with a suitable measurement device. In accordance with preferred embodiments of the present invention, the amount of color development that occurs during shear stress treatment will correspond to less than about 4.0 L* units as measured using a Macbeth Color-Eye 3000 colorimeter and dry powders having a particle size characterized in that at least 99% of the powder passes through a 100 mesh screen.

To maintain the uniformity of the color and appearance of the carrageenan products and formulations containing such products, the carrageenan-containing seaweed material should be fed into the extruder as a relatively dilute feedstream. Such a dilute feedstream typically leads to a final product with improved aesthetics (believed to be a result of optimal hydration of the carrageenan contained in the seaweed). Moreover, water typically does not have to be removed from the carrageenan containing seaweed product prior to feeding it into the extruder, which leads to a cost-effective process for the preparation of a carrageenan product as the seaweed is more efficiently sheared under such conditions. Wet processed seaweed can be in the form of chips, preferably about 2 cm to 5 cm.

Extrusion is a convenient method of shear stress treatment. Extrusion equipment with various designs can be used for extrusion of wet processed seaweed. Examples of extruders include, but are not limited to, twin-screw extruders such as the Clextral Model BC45 (Clextral, Inc., Tampa, Fla.) and Werner-Pfliederer Model ZSK-30 (Werner-Pfliederer Corp., Ramsey, N.J.). Selection of the appropriate equipment and extrusion conditions will be apparent to those skilled in the art in view of the examples described below.

In one embodiment of the present invention, a Clextral Model BC45 twin screw extruder is used. This extruder has eight barrels, each barrel having an internal diameter of 50 mm and a length of 200 mm. The screws are 1600 mm long, having a center-to-center distance of 45mm. Wet processed seaweed can be fed into the open top of the first barrel by a loss-in-weight twin screw feeder. Additional water may be pumped into the first barrel to adjust the solids content. The remaining barrels are equipped with induction heating coils and water circulation for temperature control. A venting option to allow the escape of steam may also be provided, preferably on the seventh barrel.

In another embodiment of the present invention, the carrageenan-containing feed material is fed into a single screw extruder that is connected to a twin screw extruder. The single screw extruder can be, for example, a Wenger Model X-85 and the twin screw extruder can be, for example, a Wenger Model TX-57 (both commercially available from Wenger Manufacturing, Inc., Sabetha, Kans.). Typically, the outlet of the single screw extruder is connected to the inlet of the twin screw extruder by, for example, an insulated, flexible pipe.

While not intending to be limiting, it is believed that in extrusion systems in which a single screw extruder feeds into a twin screw extruder, the heat generated by the single screw extruder thermally prepares the carrageenan-containing seaweed material for higher shear stress in the twin screw extruder. This heat is believed to pre-hydrate, or begin to solubilize, the carrageenan in the seaweed feed material. Other means to generate this heat can be used to thermally prepare the carrageenan-containing seaweed material, such as, for example, high-shear and/or high solids mixers.

The solids content of wet processed seaweed fed into the extruder typically is less than 25% by weight. The solids content of the processed seaweed can, for example, be about 24%. In one embodiment, the carrageenan-containing seaweed material or processed seaweed comprises about 23% solids. In another embodiment, the processed seaweed comprises about 22% solids. In a further embodiment, the processed seaweed comprises about 21% solids. In yet a further embodiment, the processed seaweed comprises about 20% solids. In a still further embodiment, the processed seaweed comprises about 18% solids. In another embodiment, the processed seaweed comprises about 16% solids. In a preferred embodiment, the solids content of the carrageenan-containing seaweed material is between about 10% and about 20% by weight. In a more preferred embodiment, the solids content of the carrageenan-containing seaweed material is between about 13% and about 17% by weight.

The extruder screw proffie is designed to provide a level of shear that is sufficient to disrupt the cellulose structure of the seaweed. A typical screw comprises five high shearing sections made up of conveying elements, mixing blocks, and reverse elements for three of the high shear sections. Conveying elements transport the processed seaweed material along the extruder. Reverse elements increase the residence time in the mixing blocks where some shearing occurs. The first, second and seventh barrels contain only conveying elements. A screw cap secures a die plate to the extruder exit leaving a relatively small air gap. The air gap may be adjusted to achieve sufficient back pressure for adequate shearing. For example, with the Clextral Model BC45, an air gap of 1.75 mm is used. Here, the die plate contains three holes, each being 6 mm in diameter.

To provide adequate shearing, a screw speed of at least about 200 rpm is needed. It is preferred that the screw speeds be at least about 500 rpm, more preferably, at least about 600 rpm.

Extrusion temperatures can be adjusted to achieve optimal and efficient extrusion. Elevated extrusion temperatures can assist in disrupting the seaweed structure, thereby liberating carrageenan from the structural components of the seaweed. A suitable extrusion temperature is at least about 90° C., and preferably about 120° C.

Preferably, the conditions inside the extruder are such that a phenomenon called "steam explosion" occurs. Steam explosion is the rapid discharge of material from the extruder die as a result of steam pressure inside the extruder. Specifically, by operating the extruder at a sufficiently high temperature and pressure, steam becomes pressurized in the extruder and, as a result, the carrageenan-containing seaweed material is rapidly discharged to atmospheric pressure through the extruder's exit die. It is believed that the trapped steam inside the extruded material expands at the die's orifice and results in a change in the morphology of the exiting material. Typically, the exiting material changes from solid strands to finely divided, highly expanded, open structured granules. Such granules have an increased surface area relative to granules formed in the absence of steam explosion.

There are several advantages to operating the extruder under conditions that promote steam explosion. One such advantage is that the increased surface area of the granular carrageenan-containing seaweed material allows the product to cool faster. Hot products often stick to each other, whereas cool products typically do not. Thus, material handling is improved when the product has an increased surface area. The increased surface area of the "steam exploded" granules also allows the granules to dry faster and to hydrate faster.

In other embodiments of the invention, the carrageenan containing seaweed feed material may be either admixed or co-processed with hydrocolloids and/or other additives to enhance functionality and/or to improve economics by lowering cost or expanding applications. For example, if the carrageenan product is intended for use in toothpaste, the carrageenan-containing feed material (e.g., processed seaweed or washed seaweed) may be admixed or co-processed with a food grade cellulosic such as cellulose, microcrystalline cellulose (MCC) and/or chemically modified cellulose such as carboxymethyl cellulose (CMC), methyl cellulose (MC), hydroxyethyl cellulose (HEC), hydroxylpropyl cellulose (HPC) and hydroxypropyl methylcellulose (HPMC), and with humectants, buffers, surfactants, emulsifiers, sequestrants, other bleaching or color agents, odor control agents and the like. Similarly, processed *Euchema cottonii*, processed *Euchema spinosum*, and *Euchema* wet seaweed feed materials may be either admixed or co-processed with one or more of (i) such cellulose, MCC and/or chemically modified celluloses; (ii) other seaweed extracts such as furcellaran, agar and alginates including their salts and/or chemically modified derivatives, e.g., propylene glycol alginate; (iii) natural gums and gum exudates, such as gum arabic and gum karaya, polymannans such as locust bean gum, guar and konjac, and plant extracts such as pectins and amidated pectins; (iv) biosynthetic gums such as xanthan, gellan and dextran; (v) proteins such as gelatin and chitin; (vi) synthetic hydrocolloids such as polyvinylpyrrolidone (PVP), carboxyvinyl polymers (e.g., Carbopol products), methylvinyl ether/maleic anhydride polymers (e.g., Gantrez AN products) and ethylene oxide polymers (e.g., Polyox products); (vii) starches, modified starches, dextrins, dextrose, sugars, surfactants, emulsifiers and salts; and/or other additives such as, for example, microreticulated proteins, microcrystalline starch, and the like. The additives may be selected to provide enhanced functionality including dispersion, hydration, solubility and other properties desired in the carrageenan-containing products of the invention and in food and other products for which the carrageenan-containing products are intended. Such additives, functionality and properties are known, as described, for example, in U.S. Pat. No. 5,502,179 at column 5, line 21 et seq. The additives may be introduced before, during, or after the shearing operation or to the carrageenan-containing product resulting from the shearing. The additives may also be co-processed with the carrageenan-containing seaweed feed material prior to or as part of the shearing operation, or may be coprocessed with the carrageenan-containing product resulting from the shearing. "Co-processing" or similar term, as used herein, means the formation of composites as contrasted with simple admixture or blending, as described, for example, in U.S. Pat. No. 5,441,753 at col. 5, line 32 et seq.

The throughput rate of wet processed seaweed can be varied. For example, when employing a Clextral Model BC45 having an air gap of 1.75 mm, the throughput rate of the wet processed seaweed is typically from about 40 pounds per hour up to about 200 pounds per hour. Generally, for a particular extruder, residence time of processed seaweed in the extruder decreases as the throughput rate increases. For example, for the Clextral extruder, a throughput rate of about 80 pounds of wet processed seaweed per hour results in a residence time of about 50 seconds. Solubility of extruded processed seaweed is generally better at lower throughput rates, presumably because of the greater residence time of processed seaweed in the extruder. Greater residence time allows for more shearing in the mixing blocks. Accordingly, improved solubility of wet processed seaweed can be obtained at higher throughput rates if the residence time is also increased. Increased residence time can be achieved by increasing the extruder length or increasing the number of reverse elements. Also, at high throughput rates, the barrels are fuller, which further enhances shearing in the mixing blocks.

Cold solubility temperature of extruded processed seaweed from *Eucheuma spinosum* is affected by the salt content of the product. Generally, for lower temperature solubility, a preferred salt is NaCl. An effective salt concentration is typically less than about 25% by weight, preferably less than about 15% by weight. More preferably, the salt concentration is between about 2% and 15% by weight. The desired salt concentration may be obtained by rinsing the processed seaweed material with water or a brine solution prior to extrusion. Processed seaweed material from *Eucheuma spinosum* seaweed, having a salt concentration of about 25%, typically has a maximum swelling temperature of about 92° C. Depending upon the extrusion conditions and the salt concentration employed in the methods of the present invention, the maximum swelling temperature may be lowered to about 10° C. to about 70° C. For example, extrusion of processed *Eucheuma spinosum* seaweed material having a sodium chloride concentration of about 10% lowers the maximum swelling temperature to about 25° C.

The carrageenan products of the present invention comprise carrageenan and acid insoluble material, and preferably have an onset of hydration below about 50° C. The carrageenan products of the present invention preferably comprise at least 70% by weight carrageenan and at least 2% acid insoluble material. In one embodiment of the present invention, the onset of hydration is below 35OC. In a further embodiment, the onset of hydration is below 25° C. In a preferred embodiment, the carrageenan product of the present invention is derived from *Eucheuma spinosum*, which affords iota carrageenan. The acid insoluble material comprises structural components of the seaweed, predominantly cellulosic material.

The carrageenan products of the present invention typically contain up to about 20% by weight water, preferably about 10% by weight. In a preferred embodiment, the carrageenan products further comprise about 2% to about 20% by weight of salt, preferably sodium chloride. It is more preferred that the carrageenan product comprise about 2% to about 5% salt.

It is preferred that the carrageenan products of the present invention have a particle size in the range of about 50 microns to about 200 microns. The desired particle size depends upon the particular application. For example, some applications, such as meats, require a very fine particle size such that the carrageenan products can fit through an injection needle, hence, a product having an average particle size on the low end of this range is typically employed. In other applications, such as, for example, toothpaste, the particle size of the carrageenan product is less important and, hence, a product having an average particle size on the high end of this range is typically employed.

The onset of hydration of a carrageenan product according to the present invention is determined by measuring the viscosity of its aqueous solution, preferably with a Brabender viscometer. As measured by a Brabender viscometer, the onset of hydration is the point at which one observes a change in slope of a curve plotting the viscosity of the solution as a function of time and temperature. To measure the onset of hydration by employing a Brabender viscometer, a test solution is prepared. The test solution preferably consists of the carrageenan product in water such as by mixing 10.0 g of the product in 490.0 g of deionized water. The cup speed on the Brabender viscometer is set at 75 rpm. More preferably, the test solutions consist of formulations representative of the particular product application intended for the carrageenan product. For example, the following formulations can be used:

Sorbitol/glycerin toothpaste elixir—8.0 g sample, 2.0 g sodium saccharin, 2.5 g tetrasodium pyrophosphate, 11.0 g sodium monophosphate, 170.0 g sorbitol, 100.0 g glycerin, 220.0 g deionized water.

Glycerin toothpaste elixir—8.8 g sample, 2.2 g sodium saccharin, 2.8 g tetrasodium pyrophosphate, 8.4 g sodium monophosphate, 242.0 g glycerin, 236.0 g deionized water.

Meat brine—7.5 g sample, 7.5 g sodium tripolyphosphate, 33.8 g dextrose, 22.5 g sodium chloride, 429.0 g deionized water.

Soft scrub elixir—4.9 g sample, 1.2 g terra alba, 12.2 g propylene glycol, 482.0 g deionized water.

Once the test solution is prepared, the Brabender viscometer performs a temperature profile to determine onset of hydration. Preferred temperature profiles for the above formulations are as follows:

| | Hold | | Heating at | Hold | | Cooling at | Hold | |
|---|---|---|---|---|---|---|---|---|
| | °C. | min. | 1.5° C./min. | °C. | min. | 1.5° C./min. | °C. | min. |
| 2% in water | 25 | 60 | 25 to 82 | 82 | 15 | | | |
| Sorbitol/glycerin elixir | 25 | 15 | 25 to 65 | 65 | 15 | 65 to 25 | 25 | 15 |
| Glycerin elixir | 25 | 15 | 25 to 71 | 71 | 15 | 71 to 25 | 25 | 15 |
| Meat brine | | | 45 to 71 | 71 | 15 | 71 to 25 | | |
| Soft scrub elixir | 25 | 60 | | | | | | |

Note:
All Brabender viscometer profiles were performed at 75 rpm.

The carrageenan products of the present invention exhibit enhanced gel-forming properties. For example, when a 2% solution of an SRC prepared according to the methods of the present invention is heated to about 50° C. and allowed to gel thereafter, the break strength of the gel is about 100 to about 250 g. By comparison, a 2% solution of processed seaweed heated to 50° C. does not form a gel and, when heated to 72° C., forms only a weak gel having a break strength of about 90 g. In comparison, a 2% solution of a carrageenan product prepared in a Clextral extruder at 120° C., at a throughput of 80 pounds per hour and having a salt concentration of about 10% NaCl, heated to 50° C., forms a gel having a break strength of about 150 g.

The carrageenan products of the present invention are further directed to a multiplicity of applications. Such applications include products made for human consumption such as, for example, meats, salad dressings, sauces, dairy products such as, for example, cream, milk ice cream, and nutritional and pharmaceutical capsules, as well as non-food industrial products such as, for example, toothpastes, cosmetics, paints, oil drilling fluids, and airplane de-icing fluids. It has been found that in any one of these product applications, a final product can be prepared wherein pure carrageenan extract has been extensively replaced with a carrageenan product according to the present invention.

For example, the carrageenan products of the present invention may be used as a binder in toothpaste formulations. Toothpaste formulations of the present invention comprises a binder, a humectant, an abrasive, and water, wherein the binder is the carrageenan product It is preferred that the binder be in a concentration of less than about 1.5% by weight of the toothpaste formulation.

In addition, the carrageenan products according to the invention can be used (either alone or with other components such as fillers, plasticizers and/or binders) to form films and other types of barriers. A barrier according to the invention is a material that separates two or more substances of interest to, for example, control and/or limit the extent to which they interact. Examples of barriers according to the invention include films, capsules and beads such as, for example, gel microbeads and the like.

Carrageenan-containing films according to the invention can be formed by depositing one or more carrageenan-containing layers upon a substrate. Such films can, for example, be in the form of a sheet or web, and can be applied or affixed to the substrate concurrently or sequentially. Carrageenan-containing capsules, as well as other types of barriers according to the invention, can be used to surround and protect various substances such as nutritionals, antioxidants, preservatives, and the like. As will be recognized, carrageenan-containing barrier materials according to the invention can be disposed upon or under a variety of other types of materials to form a multilayer structure.

Carrageenan capsules according to the invention can be either hard or soft gel capsules and can also be used to deliver finished dosage forms of active ingredients such as, for example, pharmaceutical compounds for ingestion or topical application. Such capsules also can be used to deliver component(s) in a process at a critical phase of manufacturing the final product. Examples of the types of soft-gel capsules that can be made with the carrageenan products produced according to the invention can be found in U.S. Pat. No. 6,214,376 and International Publication No. WO 01/03677 A1, both of which are herein incorporated by reference. When the carrageenan products of the invention are used in hard gel capsule applications, the texture of the carrageenan-containing capsule wall can be controlled, as recognized by those skilled in the art, through component selection. Gel beads used to deliver component(s) in manufacturing processes such as, for example, to immobilize enzymes for use in non-aqueous enzymatic reactions, are described in U.S. Pat. Nos. 6,268,191 and 5,662,840, both of which are herein incorporated by reference.

Carrageenans produced in accordance with the present invention can be used in a variety of manufacturing processes to form delivery systems such as, for example, the carrageenan-containing capsules and gel beads described above. Such delivery systems can be made, for example, by joining previously-manufactured, flexible, carrageenan-containing strips, by casting a uniform carrageenan-containing coating around liquid component (dual nozzle method), or by spraying a carrageenan-containing system as a liquid and then initiating film/wall formation. Numerous other methods for capsule/film/barrier formation known to those skilled in the art are included in the scope of the present invention.

Barriers according to the invention can incorporate colorants, flavorants, and volatile compounds suitable for use in flavor delivery, masking, or neutralization. Such additional substances typically are included to modify the overall presentation of the dosage form to the user. Ratios of the additional substances to the carrageenan products of the present invention can also be used to control/modify the structural integrity, properties, and functions of the finished film, barrier, capsule, bead, or caplet. For example, variable dissolution rates can be achieved which, in turn, can allow timed delivery of the various components. Examples of additional substances that can be used to modify the carrageenan structure are: starches (native, modified and/or of controlled reduced molecular weight, microcrystalline, and the like), polyols, hydrocolloids, proteins (native, polypeptides, amino acids, enzymes, and combinations, thereof), cellulosic materials of various sources, sizes and microcrystallinity, sugars (mono- and polymerized), and the like.

The following examples illustrate the present invention and are not intended to limit the same. In this specification and claims, all parts and percentages are by weight, all temperatures are in degrees Celsius, and all pressures are in mm Hg, unless otherwise specified.

EXAMPLES

Comparative Examples 1-3

Effects of Feedstock Extrusion Versus % Moisture

Materials: The primary raw material used in Examples 1-3 was we alkali modified *cottonii* seaweed. The material was made to food grade standards including (1) removing plastic ties from the weed prior to processing and (2) bleaching the weed to remove color. Two batches of raw materials having different moisture contents were obtained, one batch had about 85% moisture, while the other batch had about 77% moisture. Furthermore, washed, chopped and dried *cottonii* having a moisture content of about 27% was also used. Processes according to the present invention were performed using feedstocks having about 86%, about 79% and about 74% moisture content, obtained by blending these three *cottonii* materials. A small ribbon blender (estimated at approximately 8-10 ft$^3$ capacity) was used to prepare the feedstocks by combining the three *cottonii* raw materials and additional water as required. Materials were blended for 10-15 minutes to equilibrate.

Extrusion system: The extrusion system employed was as follows:
Feeder/feedrate—AccuRate brand device commercially available from AccuRate, Whitewater, Wis., calibrated to 54 kg/hr using 77% moisture material;
Single screw extruder—Wenger X-20 operating at 500 rpm, exit temperature at 95-100° C.;
Twin screw extruder—Wenger TX-52 operating at 454 rpm, exit temperature at 120-180° C.;
Twin screw exit die plate—single 4 mm diameter hole;
Twin screw exit pressure manually adjusted with die throttle valve to maintain maximum exit pressure and barrel fill (retention time).

Example 1

Extrusion of High Moisture Content Feedstock

Processing: Extruder conditions were stable and exit conditions at the TX-52 were easy to maintain.

Moisture content: Final measurements of percentage moisture in the feedstocks were determined by employing either a moisture balance such as, for example, a Denver Instruments IR200 or a Mettler LJ16 or air oven methods. A typical air oven method is to dry a sample at about 60° C. overnight and determine the % moisture by a simple calculation based on the differences of the wet and dry materials. A slight difference was observed between these two methods. As seen in the table below, since the difference and standard deviation are small, all subsequent discussions will be based on the Average data.

| Feedstock % moisture content | | | | |
|---|---|---|---|---|
| Feed | IR200 | 60° oven | Average | Std. Dev. |
| A | 86.11 | 86.42 | 86.27 | 0.22 |

Brabender hydration profiles: Product hydration rate for the feedstock having a moisture content of about 86% was determined in a Brabender Viscograph B using the specific test method detailed in U.S. Pat. No. 5,502,179 at, for example, column 4, lines 17-23. The results are shown in FIG. 1. There was no significant change in the temperatures of either hydration peak as a function of feedstock. Maximum viscosity of 148-160 BU was observed with feedstock having about 86% moisture content (FIG. 1).

| | Brabender hydration peaks | | | |
|---|---|---|---|---|
| | | 1$^{st}$ peak | | 2$^{nd}$ peak |
| Feed | % moisture | ° C. | BU | ° C. | BU |
| A | 86.27 | 64 | 160 | 80 | 148 |

BU = maximum attained viscosity in Brabender Units

Example 2

Low Moisture Content Feedstock

Processing: Testing was performed to compare the results obtained using feedstocks with moisture contents lower than those used in accordance with the present invention. No significant processing differences between the three *Cottonii* feedstocks was observed. Extruder conditions were stable and exit conditions at the TX-52 were easy to maintain for all three products. The lower moisture feedstocks produced drier products at the exit. Exit at the twin screw increased with the lower moisture feedstocks.

Moisture content: final measurements of % moisture in the feedstocks showed a slight difference between the IR200 and the air oven method. As the difference and standard deviation are small, all subsequent discussions will be based on the Average data.

| | Feedstock % moisture content | | | |
|---|---|---|---|---|
| Feed | IR200 | 60° oven | Average | Std. Dev. |
| B | 78.85 | 79.60 | 79.23 | 0.53 |
| C | 73.58 | 74.47 | 74.03 | 0.63 |

Brabender hydration profiles: Product hydration rates for feedstocks having moisture contents of 79% and 74% were determined in a Brabender Viscograph E using the specific test method detailed in U.S. Pat. No. 5,502,179 at, for example, column 4, lines 17-23. No significant difference in hydration behavior was apparent. There was no significant change in the temperatures of either hydration peak as a function of feedstock. However, a decrease in maximum viscosity with a decrease in feedstock moisture indicated a loss of viscosity due to the high shearing effect of the process of the invention. While the maximum viscosity observed with feedstock having about 86% moisture content was 148-160 BU, the maximum viscosity observed with a lower feedstock moisture content of about 79% and about 74% was 102-104 BU and 52-68 BU, respectively (FIG. 1). This loss of functionality indicates the process of the present invention is configured to best handle feedstocks with greater than 80% moisture content.

| | | Brabender hydration peaks | | | |
|---|---|---|---|---|---|
| | | $1^{st}$ peak | | $2^{nd}$ peak | |
| Feed | % moisture | °C. | BU | °C. | BU |
| B | 79.23 | 63 | 102 | 82 | 104 |
| C | 74.03 | 61 | 68 | 80 | 52 |

BU = maximum attained viscosity in Brabender Units

Example 3

Effect of Feedstock Moisture Content on Color

The color of the powder was measured using a Macbeth ColorEye 3000 colorimeter on material that was ground to 99.5% through 100 mesh (150 micron). Powder color is reported in L* units; the lower the L*, the darker the powder. Typical product specifications have L* greater than 74-75. A significant change in product powder color was observed as a function of feedstock moisture content. A substantial darkening of product color was observed upon decreasing the moisture content of the feedstock from about 85% to about 80%. As seen from the table below, a feedstock moisture content of about 86% afforded a product having L* (powder color) of 79.5. Powder color is an aesthetic quality that is important to customer acceptance of carrageenan products that are used in food products; lighter colored products are preferred A change of 1½-2 L* units is readily noticeable by an untrained eye. Knowledgeable end users can detect an even smaller change in L*.

| | | Powder color, L* | | |
|---|---|---|---|---|
| Feed | % MC | Product | Feed | Δ |
| A | 86.27 | 79.520 | 83.294 | 3.774 |
| B | 79.23 | 74.647 | 78.550 | 3.903 |
| C | 74.03 | 73.184 | 79.655 | 5.625 |

Example 4

An alkali-dipped *Chondrus* feedstock was also used to test the effect of a high shear extrusion system on a different seaweed. This *Chondrus* material was made by (1) washing the weed in fresh water, (2) chopping the weed to the desired size; (3) drying in a 60° C. air oven; and (4) adjusting the moisture content to about 30% by spraying with a 0.2N NaOH solution. The moisture content of the *Chondrus* feedstock was adjusted to about 29.9% (measured) with water. Measured moisture content before adjustment (as shipped) was 22%. The material was too large to uniformly feed through the AccuRate so a Fitz mill was used to chop the material to about ¼-½" pieces. A small ribbon blender (estimated at approximately 8-10 ft³ capacity) was used to prepare the feedstocks. Materials were blended for 10-15 minutes to equilibrate. This *Chondrus* material had a moisture content of about 29.94% (Actual % moisture). Actual % moisture was measured using a Denver Instruments IR200 moisture balance set at 150° C.

Extrusion system: the extrusion system employed was as follows:

Feeder/feedrate—AccuRate brand device commercially available from AccuRate, Whitewater, Wis., calibrated to 54 kg/hr using 77% moisture material;
Single screw extruder—Wenger X-20 operating at 500 rpm, exit temperature at 95-100° C.
Twin screw extruder—Wenger TX-52 operating at 454 rpm, exit temperature at 120-180° C.;
Twin screw exit die plate—single 4 mm diameter hole;
Twin screw exit pressure manually adjusted with die throttle valve to maintain maximum exit pressure and barrel fill (retention time).

Processing: The screw elements of the X-20 in the carrageenan extraction process are configured for maximum shear and, therefore, were not able to convey the high solids level *chondrus* through the extruder. A very dense, solid plug of material formed near the end of the X-20 and stopped all flow. This plug showed evidence of charring from the thermomechanical energy input from the extruder and from autocatalytic acid hydrolysis from carrageenan decomposition. The single screw extruder was bypassed and the feed was fed directly to the TX-52. Although the twin screw extruder was able to convey the feed, product exiting the machine was charred (with exit temperature up to 180° C.). Both screw speed and barrel temperature were reduced to 170 RPM and 100-130° C., respectively, and with cooling water on the last barrel) to minimize charring. It was, however, suspected that the extrusion conditions were still too severe to completely prevent any carrageenan degradation.

Brabender hydration profiles: Brabender hydration profiles confirmed that the carrageenan contained in the *Chondrus* was destroyed during extrusion. Although the *Chondrus* feedstock showed development of a typical Brabender viscosity peak, the extruded *Chondrus* showed a complete lack of viscosity. No further testing was performed.

These results illustrate that the process of the invention is a high shear process suitable only for feedstocks with high moisture content. A model of the process suggests that a high moisture level contributes to (1) a lower feed density; (2) partial hydration of the carrageenan in the single screw extruder, (3) increased lubrication at the screw-feed interface; (4) increased thermal energy absorption; and (5) temperature conditions that minimize carrageenan degradation It appears that all of these factors are required to successfully operate the process.

As demonstrated in Examples 1-3, the *Cottonii* products extruded under constant process conditions from feedstocks containing between 75-85% moisture were generally very similar. However, there were two important functionality differences. First, significant loss in product viscosity occurs as the moisture content of the feedstock drops below 80%. A lower product viscosity is generally unacceptable for a SRC that is used as a thickening agent. Next, significant darkening of product powder color occurs as the moisture content of the feedstock drops below 80%. A darker powder color is unacceptable for SRC that is used in food products whose color must be maintained almost colorless or white.

Furthermore, high solids feedstocks, such as the 30% moisture *Chondrus,* are not generally suitable for the processes of the invention. The high shear extrusion conditions were too severe in the absence of adequate lubrication by the water in the feed. In low moisture feedstocks, the carrageenan in the weed is completely degraded in the process.

Example 5

Extrusion of Base-Treated *Eucheuma cottonii* Feedstock Using a Single and Twin Screw Extruder:

Starting Material:
1. Modify *Eucheuma cottonii* feedstock through a standard PES process and drain.
2. Wash the modified *Eucheuma cottonii* feedstock in cold water for 30 minutes and drain. Repeat.
3. Bleach for 30 minutes in 0.17% Ca(OCl)$_2$ and drain.
4. Wash in cold water for 30 minutes and drain.

Moisture content of the starting material was 86-87%. KCl content was 0.5-3.0%. The *cottonii* was chopped to ½" pieces before bleaching.

Pre-pasting: The chopped *cottonii* was metered into a Wenger X-85 single screw extruder using an Accu-rate feeder. Temperature in the single screw was controlled to target a material exit temperature of 95° C. by steam circulating through eight individual heads. Processed *cottonii* was heated and mixed in the single screw to breakdown seaweed structure until paste was smooth. The seaweed was then conveyed to a twin screw extruder through a 1.5" diameter pipe engineered to achieve a closed system transfer.

Extrusion: After pre-pasting, processed *cottonii* material was fed into an 8 barrel Wenger TX-57 co-rotating, intermeshing, twin screw extruder. The high shear screw configuration used for this sample is proprietary to Wenger. Temperature control was separated into 5 zones. The last four barrel zones were heated with steam.

Extrusion exit: A valve just before the 4 mm, 1 hole die at twin screw exit controlled backpressure to ensure steam explosion of extruded processed *cottonii* material out of the machine. The extruded *cottonii* resembled fine breadcrumbs as it exited the extruder.

Samples: As sample exited the extruder it was transferred to a collection bin by a pneumatic conveyor. This tumbled and cooled product to prevent it from sticking together. It was then dried in a Wenger Series VII 3-stage belt dryer.

Process settings and readings:

| Accu-rate feeder | Feed rate | 147 kg/nr |
|---|---|---|
| Single screw | Exit temp. | 95° C. |
| | Screw speed | 600 rpm |
| | Residence time | 1 minute |
| | Motor load | 22% full load |
| Twin screw | Barrel temp zones (° C.) | 46, 125, 129, 140, 140 |
| | Exit temp. | 116° C. |
| | Screw speed | 605 rpm |
| | Exit rate | 147 kg/hr |
| | Residence time | 1.5 minutes |
| | Motor load | 6% full load |

Testing: Dried sample was ground to at least 95% through 100 mesh for testing. Table 1 shows general quality testing of the extruded *cottonii* compared to the starting material to show that no carrageenan degradation occurred during extrusion. Table 2 shows solubility improvements of the extruded *cottonii* over the starting material during a 2% in water Brabender profile. Table 3 shows solubility improvements of the extruded *cottonii* over the starting material in a meat brine elixir Brabender profile.

TABLE 1

General Quality testing

| Test | Processed PBS *cottonii* st. mat. | Extruded PES *cottonii* |
|---|---|---|
| Moisture content (%) | 86-87 | 85.96 |
| Viscosity (cP) | 85 | 91 |
| pH | 9.00-9.60 | 9.03 |
| KCl (%) | 0.5-3.0 | 2.80 |
| Mesh (% through 100 mesh) | 90-100 | >95 |

TABLE 2

Brabender Analysis - Solubility Testing - 2% in water

| | | Processed PES *cottonii* st. mat. | Extruded PES *cottonii* |
|---|---|---|---|
| Begin swell: | C | 68 | 48 |
| | BU | 2 | 3 |
| 1$^{st}$ peak | C | no peak | 52 |
| | BU | no peak | 89 |

TABLE 2-continued

Brabender Analysis - Solubility Testing - 2% in water

|  |  | Processed PES cottonii st. mat. | Extruded PES cottonii |
|---|---|---|---|
| $2^{nd}$ peak | C | 77 | 65 |
|  | BU | 12 | 35 |
| End 82° C. hold | BU | 8 | 29 |

TABLE 3

Brabender Analysis - Solubility Testing - Meat Brine Elixir

|  |  | Processed PES cottonii st. mat. | Extruded PES cottonii |
|---|---|---|---|
| Begin swell: | C | 71 | 66 |
|  | BU | 19 | 2 |
| $1^{st}$ peak | C | no peak | 68 |
|  | BU | no peak | 19 |
| $2^{nd}$ peak (71° C.) | BU | 35 | 17 |
| End 71° C. hold | BU | 35 | 15 |

Example 6

Extrusion of Base-Treated *Eucheuma cottonii* Feedstock Using a Twin Screw Extruder Starting material: Processed *cottonii* starting material was prepared by putting *Eucheuma cottonii* seaweed though a standard PES process, chopping PES *cottonii* to ½ inch chips, drying, and then grinding to 100 mesh.

Extrusion: Powdered processed *cottonii* was fed from a hopper into a 12 barrel Werner-Pfleiderer ZSK-30 co-rotating, intermeshing, twin screw extruder. Total length L/D ratio was 37. Water was sprayed into the feed section along with the Processed *cottonii* to create a mixture at 80% moisture. The high shear screw configuration used for this sample is proprietary to Werner-Pfleiderer. Heating and cooling were controlled in barrels 4 thru 10 with electric heating and water cooling.

Extrusion exit: No die plate was put onto screw exit. Material exited with the appearance of elastic, ground, uniform bits.

Samples: Sample was spread into pans to cool, then dried overnight in a 60° C. oven.

Process settings and readings:

| Feeder | Feed rate | 9 kg/hr |
|---|---|---|
| Twin screw | Barrel temps. (° C.) | 25, 82, 90, 90, 89, 89, 90, 90, 90, 90 |
|  | Exit temp. | 90° C. |
|  | Screw speed | 500 rpm |
|  | Exit rate | 9 kg/hr |

Testing: Dried sample was ground to 91% through 100 mesh for testing. Table 4 shows general quality testing of the extruded Processed *cottonii* compared to the starting material, to show that no carrageenan degradation occurred during extrusion. Table 5 shows solubility improvements of the extruded Processed *cottonii* over the starting material during a 2% in water Brabender profile.

TABLE 4

General Quality Testing

| Test | Processed PES cottonii starting material | Extruded PES cottonii |
|---|---|---|
| Moisture content (%) | 6 | not measured |
| Viscosity (cP) | 160 | 55 |
| 101 gel (gms breakforce) | 491 | 435 |
| KCl (%) | 1.5 | 1.4 |
| Mesh (% thru 100 M) | 90-100 | 91 |

TABLE 5

Brabender Analysis - Solubility Testing - 2% in Water

|  |  | Processed PES cottonii starting material | Extruded PES cottonii |
|---|---|---|---|
| Begin swell: | C | 59 | 56 |
|  | BU | 12 | 12 |
| $1^{st}$ peak: | C | no peak | 59 |
|  | BU | no peak | 24 |
| $2^{nd}$ peak: | C | 78 | 75 |
|  | BU | 60 | 28 |
| At 82° C.: | BU | 59 | 27 |

Example 7

Extrusion of Base-Treated *Eucheuma spinosum* Feedstock Using Single and Twin Screw Extruders Starting material: PES *spinosum* starting material was prepared by putting *Eucheuma spinosum* seaweed through the following process:
1. Soak seaweed in 25% NaCl for 1 hour and drain.
2. Modify in 7.9% NaCl, 2.86% NaOH for 2 hours at 45° C. and drain.
3. Wash in 9% NaCl for 30 minutes and drain.
4. Bleach in 0.25% NaOCl for 30 minutes and drain
5. Wash in 6% NaCl for 30 minutes and drain.
6. Wash in cold water and drain.

Moisture content of the PES *spinosum* starting material was 78-82%. NaCl content was 11-15%. The *spinosum* was chopped to ½" pieces before bleaching.

Pre-pasting: The chopped PES *spinosum* was metered from an Accu-rate feeder into a Wenger X-85 single screw cruder. Temperature in the single screw was controlled to target a material exit temperature of 100° C. by steam circulating through eight individual heads and by steam injection. PES *spinosum* was heated and mixed in the single screw to breakdown seaweed structure and paste until relatively smooth. Material was then conveyed to a twin screw extruder through a 1.5" diameter pipe engineered to achieve a closed system transfer.

Extrusion: As PES *spinosum* paste exited from the single screw, it was fed into an 8 barrel Wenger TX-57 co-rotating, intermeshing, twin screw extruder. The high shear screw configuration used for this sample is proprietary to Wenger. Temperature control was separated into 5 zones. The last 4 zones were heated with steam.

Extrusion exit: A valve just before the 4 mm 1 hole die at twin screw exit controlled backpressure to ensure steam explosion of the extruded PES *spinosum* material out of the machine. Extruded *spinosum* exited as fine breadcrumbs.

Sample: As sample exited the extruder it was transferred to a collection bin by a pneumatic conveyor. This tumbled and cooled product to prevent it from sticking together. It was then dried in a Wenger Series VII 3-stage belt dryer.

Process settings and readings:

| Accu-rate feeder | Feed rate | 144 kg/hr |
|---|---|---|
| Single screw | Exit temp. | 100° C. |
| | Screw speed | 600 rpm |
| | Motor load | 17% full load |
| Twin screw | Barrel temp zones (° C.) | 48, 124, 128, 138, 136 |
| | Exit temp. | 107° C. |
| | Screw speed | 600 rpm |
| | Exit rate | 144 kg/hr |
| | Motor load | 5% full load |

Testing: Dried sample was ground to at least 95% through 100 mesh for testing. Table 6 shows general quality testing of the extruded PES *spinosum* compared to the starting material, to show that no carrageenan degradation occurred during extrusion. Table 7 shows solubility improvements of the extruded PES *spinosum* over the starting material during a 2% in water Brabender profile.

TABLE 6

General Quality testing

| Test | Processed PES *spinosum* st. mat | Extruded PES *spinosum* |
|---|---|---|
| Moisture content (%) | 78-82 | 81 |
| Viscosity (cP) | 30 | 38 |
| pH | 8.30-8.90 | 8.73 |
| NaCl (%) | 11-15 | 11.72 |
| Mesh (% through 100 mesh) | 90-100 | >95 |

TABLE 7

Brabender Analysis - Solubility Testing - 2% in water

| | | Processed PES *spinosum* st. mat | Extruded PES *spinosum* |
|---|---|---|---|
| Hold at 25° C.: | | | |
| Start | BU | no peak | 184 |
| End | BU | no peak | 177 |
| Heating peak: | C | 65 | no peak |
| | BU | 26 | no peak |
| End 82° C. hold | BU | 26 | 26 |

Example 8

Extrusion of Washed, Non-Base-Treated *Eucheuma spinosum* Feedstock Using Single and Twin Screw Extruders Starting material: Washed *spinosum* starting material was prepared from *Eucheuma spinosum* seaweed in the following manner:
1. Soak in cold water for 30 minutes and drain.
2. Soak in cold 1.5% NaCl and drain.
3. Press out excess water in a Wilmes press.

Moisture content of washed *spinosum* starting material was 85-86%. NaCl content was 8%. The washed *spinosum* was chopped to ½" pieces.

Pre-pasting: The chopped, washed *spinosum* was metered from an Accu-rate feeder into a Wenger X-20 single screw extruder. Temperature in the single screw was controlled to target a material exit temperature of 95° C. by steam circulating through eight individual heads. Washed *spinosum* was heated and mixed in the single screw to breakdown seaweed structure and partially paste. Pre-pasted, washed *spinosum* was relatively smooth, but had some remaining weed bits. Material was then conveyed to a twin screw extruder through a 1.5" diameter insulated pipe.

Extrusion: As washed *spinosum* paste exited from the single screw, it was fed into an 8 barrel Wenger TX-52 co-rotating, intermeshing, twin screw extruder. The high shear screw configuration used for this sample is proprietary to Wenger. Extruder barrels 4 through 6 were heated with circulating hot oil and steam was injected into barrels 3 and 4.

Extrusion exit: A valve just before the 4 mm, 3 hole die at twin screw extruder exit controlled backpressure to ensure steam explosion of extruded, washed *spinosum* material out of the machine. Extruded, washed *spinosum* exits as a mixture of wet granules and viscous paste.

Samples: Care was used in collecting extruded, washed *spinosum* material to ensure that sample did not stick together. Sample was spread into pans to cool, before being dried overnight in a 60° C. oven.

Process settings and readings:

| Accu-rate feeder | Feed rate | 33 kg/hr |
|---|---|---|
| Single screw | Exit temp. | 96° C. |
| | Screw speed | 100 rpm |
| | Motor load | 11% full load |
| Twin screw | Barrel temps. (° C.) | 73, 73, 95, 119, 119, 120, 120, 120 |
| | Exit temp. | 135° C. |
| | Screw speed | 472 rpm |
| | Exit rate | 33 kg/hr |
| | Motor load | 9% full load |

Testing: Dried sample was ground to 91% through 100 mesh for testing. Table 8 shows general quality testing of the extruded, washed *spinosum* compared to the starting material, to show that no carrageenan degradation occurred during extrusion. Table 9 shows improved solubility of the extruded, washed *spinosum* over the starting material in 65° C., sorbitol/glycerin toothpaste elixir Brabender profile. Table 10 shows solubility improvements of the extruded, washed *spinosum* over the starting material in 71° C., glycerin toothpaste elixir Brabender profile.

TABLE 8

General Quality Testing

| Test | Washed *spinosum* starting material | Extruded washed *spinosum* |
|---|---|---|
| Moisture content | 85-86 | 85.9 |
| Viscosity (cP) | 50-60 | 41 |
| pH | 7.5-8.5 | 7.8 |
| NaCl (%) | 6-10 | 6.2 |
| Mesh (% thru 100 M) | 90-100 | 91 |

TABLE 9

Brabender Analysis - Solubility Testing - 65° C.
Sorbitol/Glycerin Toothpaste Elixir

|  |  | Washed spinosum starting material | Extruded washed spinosum |
|---|---|---|---|
| Begin swell: | C | 62 | 44 |
|  | BU | 30 | 45 |
| End 65 C. hold: | BU | 44 | 122 |
| Cooled: | C | 25 | 25 |
|  | BU | 540 | 850 |

TABLE 10

Brabender Analysis - Solubility Testing -
71° C. Glycerin Toothpaste Elixir

|  |  | Washed spinosum starting material | Extruded washed spinosum |
|---|---|---|---|
| Begin swell: | C | 66 | 37 |
|  | BU | 23 | 40 |
| End 71 C. hold | BU | 81 | 89 |
| Cooled: | C | 26 | 37 |
|  | BU | 695 | 651 |

Example 9

Extrusion of Base-Treated *Eucheuma spinosum* Feedstock Using a Twin Screw Extruder Starting material: PES *spinosum* starting material was prepared by putting *Eucheuma spinosum* seaweed though the following process:
1. Modify in 1.0M NaOH, 3.1M NaCl for 6 hours at 45° C. and drain.
2. Follow modification with two cold, 30-minute 5% NaCl rinses. 3. Neutralize pH in the first rinse.
4. This sample was given an additional 30-minute cold water soak at the trial before extruding.

Moisture content of PES *spinosum* starting material was 83%. The PES *spinosum* was chopped to ½" pieces.

Extrusion: The chopped PES *spinosum* was metered from a volumetric feeder into a 9 barrel Clextral BC-45 co-rotating, intermeshing, twin screw extruder. The high shear screw configuration used for this sample is proprietary to Clextral. Heating and cooling were controlled on the last eight barrels by induction coils and cooling water.

Extrusion exit: Exit temperature was measured just before a 3 mm, 3 hole cooling die plate. Extruded PES *spinosum* exited as opaque, sticky, spreadable strands.

Samples: Sample was belt conveyed for approximately 15 seconds to cool before collecting in pans. The sticky material tended to clump together even when cool, so it had to be manually broken into smaller bits before drying overnight in a 60° C. oven.

Process settings and readings:

| Volumetric feeder | Feed rate | 54 kg/hr |
|---|---|---|
| Twin screw | Barrel temps. (° C.) | 25, 128, 189, 175, 140, 142, 124, 99, 79 |
| Exit temp. |  | 81° C. |
| Screw speed |  | 550 rpm |
| Exit rate |  | 54 kg/hr |
| Residence time |  | 2.0 minutes |
| Motor load |  | 11 amps |

Testing: Dried sample was ground to 94% through 100 mesh for testing. Table 11 shows general quality testing of the extruded PES *spinosum* compared to the starting material, to show that no carrageenan degradation occurred during extrusion. Table 12 shows solubility improvements of the extruded PES *spinosum* over the starting material during a 2% in water Brabender profile.

TABLE 11

General Quality Testing

| Test | PES spinosum starting material | Extruded PES spinosum |
|---|---|---|
| Moisture content (%) | 83.0 | 82.5 |
| Viscosity (cP) | 28 | 32 |
| pH | 9.90 | 9.10 |
| NaCl (%) | not measured | 7.47 |
| Mesh (% thru 100M) | 90-100 | 97 |

TABLE 12

Brabender Analysis - Solubility Testing - 2% in Water

|  |  | PES spinosum starting material | Extruded PES spinosum |
|---|---|---|---|
| Hold at 25° C. |  |  |  |
| Start | BU | 8 | 35 |
| End | BU | 9 | 122 |
| 1st peak: | C | 30 | 30 |
|  | BU | 9 | 65 |
| 2nd peak: | C | 60 | 60 |
|  | BU | 27 | 27 |
| End 82° C. hold: | BU | 59 | 13 |

Examples 10 and 11

Examples 10 and 11 demonstrate the applicability of the carrageenan products of the present invention as an ingredient in toothpaste formulations. Specifically, toothpaste formulations of the present invention are evaluated for efficacy of the carrageenan product as a carrageenan binder in the toothpaste. The efficacy of a carrageenan binder in a toothpaste formulation is determined by measuring the strength, stability, and texture of the toothpaste formulation. A traditional method for measuring toothpaste strength, stability, and texture is by using a Cuban rating system wherein the toothpaste strands are squeezed over a Cuban rack. Ability of the strands to stay suspended between bars with numbered size increments determines the 1 to 12 rating given to the toothpaste. Measurements are typically taken over a period of 9 weeks. More particularly, measurements are taken after 1 day, 1 week, 3 weeks, 6 weeks, and 9 weeks at storage temperatures of about 25° C. and 50° C., to determine toothpaste strength, stability, texture and degree of "heat shock." Heat shock is defined as a change (increase of decrease) in the strength of the toothpaste upon storage at 50° C. A change of more than 3 Cuban ratings is considered undesirable. A disadvantage of the Cuban test is that the toothpaste must be prepared and the measurements be taken over a period of 9 weeks to make a quality determination for a particular carrageenan sample.

The toothpaste formulations according to the present invention are examined for carrageenan solubility using a Brabender Viscograph test wherein a toothpaste "elixir" is used to examine carrageenan solubility in the presence of other toothpaste ingredients. The toothpaste "elixir" formula contains ingredients in the same ratios as that of a typical toothpaste formulation, except that the "elixir" lacks the bulking agent, the foaming agent and the flavor oil. Brabender temperature profiles typically focus on conditions for carrageenan solubility. It was determined that the Brabender toothpaste "elixir" test was an excellent predictor of the performance of the carrageenan product of the present invention in a toothpaste formulation. The advantage of the Brabender test used in the present invention, relative to the traditional Cuban rating system, is that the Brabender test decreases the time required to make functional quality determinations from 9 weeks to a few hours.

In the following examples, toothpaste "elixirs" were analyzed using Brabender viscographs to examine carrageenan solubility in the presence of toothpaste ingredients. The toothpaste elixir formula contained ingredients in the same ratios as that of a typical toothpaste system except that the bulking agent, the foaming agent and the flavor oil were absent in the elixir formula. Brabender temperature profiles typically focus on conditions for carrageenan solubility in order to understand the solubility potential for carrageenan under the application-specific process conditions. The Brabender toothpaste elixir formula and temperature profiles developed for use in the work discussed here were designed to track solubility of carrageenan products in toothpaste systems focusing on toothpaste process conditions.

Example 10

Toothpaste Elixir

In this case, toothpaste elixir testing was done at process temperatures of both 65° C. and 71° C.

Toothpaste Cuban ratings measure strength of prepared toothpaste. Degree of heat shock is determined by the change in toothpaste strength after storage at 50° C. for three days. The Brabender toothpaste elixir test contributes additional information regarding the process of making the toothpaste: when solubility takes place (at what time and temperature), whether hydration is complete, viscosity contribution during processing, and viscosity contribution to the final product.

Tables 13 and 14 compare the slope and viscosity of the toothpaste elixir solubility curve during the hold at elevated temperature to the Cuban rating changes during storage of actual toothpaste.

Table 13 compares washed *spinosum*, extruded washed *spinosum*, and a toothpaste extract blend at a process temperature of 65° C. The positive slope during the 65° C. hold for all three samples suggests that none of them are fully solubilized. Comparison of washed *spinosum* to extruded washed *spinosum* shows a small difference in slope between the two, but a significant improvement in the Cuban ratings for the extruded and washed *spinosum*, indicating improvement from extrusion. Comparison of the extruded and washed *spinosum* to the toothpaste extract blend shows similar toothpaste Cuban ratings for 1 day, 25° C., even though there are large differences in process viscosity. The slope difference for these two samples is highly significant, explaining the differences in heat shock. The extract, with a slope of 28.8 BU/minute, exhibits an increase of 4 Cuban units, from 5 to 9; whereas, the extruded and washed *spinosum*, with a slope of 2.0 BU/minute, shows an increase of only 2 Cuban units, from 6 to 8. Although an increase of 2 Cuban units is considered acceptable, an increase of 4 Cuban units is unacceptable.

Table 14 compares the same three samples at a process temperature of 71° C. The negative slopes of the extruded and washed *spinosum* and the toothpaste extract indicate they are fully solubilized at this higher process temperature. The higher Cuban ratings also reflect this, as does the lack of heat shock for these three samples.

The Brabender elixir test results also provide information regarding the difference in process viscosity, which Cuban ratings do not. Although the extruded and washed *spinosum* compares closely to the toothpaste extract in Cuban units and a high final, cooled viscosity, process viscosity is significantly lower for the extruded and washed *spinosum*, as indicated by the Brabender elixir test results. In this case, the low process viscosity is advantageous in typical toothpaste preparation

TABLE 13

Toothpaste Elixir Solubility Profile Compared to Toothpaste Cuban Rating, 65° C. Processing

| | Begin 65° C. (BU) | End 65° C. (BU) | End 25° C. (BU) | Slope of curve @ 65° C. (BU/min.) | 1 day Cuban, 25° C. | 2 day Cuban, 50° C. |
|---|---|---|---|---|---|---|
| Washed *spinosum* | 29 | 44 | 538 | 1.0 | 3 | 3 |
| Extruded, washed *spinosum* | 92 | 122 | 837 | 2.0 | 6 | 8 |
| Toothpaste Extract Blend | 293 | 725 | 1216 | 28.8 | 5 | 9 |

TABLE 14

Toothpaste Elixir Solubility Profile Compared to Toothpaste Cuban Rating, 71° C. Processing

| | Begin 71° C. (BU) | End 71° C. (BU) | End 25° C. (BU) | Slope of curve @ 71° C. (BU/min.) | 1 day Cuban, 25° C. | 2 day Cuban, 50° C. |
|---|---|---|---|---|---|---|
| Washed *spinosum* | 47 | 71 | 850* | 1.6 | 12 | 12 |
| Extruded, washed *spinosum* | 101 | 89 | 850* | −0.8 | 11 | 12 |
| Toothpaste Extract Blend | 850 | 740 | 1416 | −7.3 | 6 | 6 |

*Extrapolated from curve.

Example 11

Glycerin/Sorbitol Chalk Toothpaste

Two extruded, washed *spinosum* samples (EWS-1 and EWS-2) were tested in inexpensive, glycerin/sorbitol chalk toothpaste at a 65° C. process temperature. The results were excellent and showed no heat shock Table 15 compares the Cuban ratings of the two toothpastes.

TABLE 15

Toothpaste Performance in Chalk-Based Toothpaste

|  | 1 day Cuban, 25° C. | 2 day Cuban, 50° C. |
| --- | --- | --- |
| EWS-1 | 6 | 5 |
| EWS-2 | 7 | 6 |

Results (from Examples 10 and 11):
(1) Using a toothpaste elixir that mimics a toothpaste is a means to not only gain information about performance of stabilizers in a final product, but also important information regarding performance during the toothpaste processing.
(2) The occurrence of toothpaste heat shock is directly proportional to increased steepness or positive slope of the solubility curve during the process hold at an elevated temperature.
(3) Differences in product performance for a sample processed at two different temperatures can be readily observed and explained by the solubility information provided by an elixir Brabender profile.
(4) Process viscosity is not directly proportional to final toothpaste strength.
(5) The Brabender toothpaste elixir test is an excellent predictor of carrageenan performance in actual toothpaste. It can reduce the time it takes to make functional quality determinations from weeks or days to hours.
(6) Toothpaste process elixir Brabenders tests can be useful in determining process temperature limitations and ranges for any toothpaste system Analysis (based on Examples 10 and 11):

Two regions of the Brabender solubility profile are useful in predicting the toothpaste performance for a particular sample:

(1) Fifteen-minute hold at elevated temperature: The viscosity and change in viscosity over time (slope) of the solubility curve during the hold at an elevated temperature is a strong indicator of potential toothpaste heat shock. The steeper this slope, the more chance of heat shock. The flatter the slope, the less chance of heat shocks
(2) Final cooling to 25° C.: The final cooled viscosity of the processed elixir indicates the potential viscosity contribution a carrageenan sample can make to toothpaste. This final cooled viscosity is not the same as the process viscosity.

What is claimed is:

1. A semi-refined iota carrageenan-containing product made by a process comprising subjecting a carrageenan-containing seaweed material having a solids content of less than 25% by weight to a shear stress treatment to provide said carrageenan-containing product, wherein said process further comprises drying said carrageenan-containing product to produce a dried carrageenan-containing product and grinding said dried carrageenan-containing product, and wherein said product has a color of greater than about 74 L* units as measured using a Macbeth ColorEye 3000 colorimeter and a particle size characterized in that at least 99% of the powder passes through a 100 mesh screen.

2. The product of claim 1 having an onset of hydration below about 50° C. as measured with a Brabender viscometer as a 2% by weight solids aqueous solution.

3. The product of claim 1 comprising about 1% to about 20% by weight of a salt.

4. A toothpaste formulation comprising a binder, a humectant, an abrasive, and water, wherein the binder comprises the carrageenan-containing product according to claim 1.

5. The toothpaste formulation of claim 4 wherein the binder comprises less than about 1.5% by weight of the toothpaste formulation.

* * * * *